US00PP08113P

United States Patent [19]

VandenBerg

[11] Patent Number: Plant 8,113

[45] Date of Patent: Jan. 19, 1993

[54] CHRYSANTHEMUM PLANT NAMED CUMBIA

[75] Inventor: Cornelis P. VandenBerg, Salinas, Calif.

[73] Assignee: Yoder Brothers, Inc., Barberton, Ohio

[21] Appl. No.: 715,634

[22] Filed: Jun. 14, 1991

[51] Int. Cl.[5] ..... A01H 5/00

[52] U.S. Cl. ..... Plt./74.1

[58] Field of Search ..... Plt./74, 74.1

[56] References Cited

U.S. PATENT DOCUMENTS

P.P. 3,945 8/1976 Jessel, Jr. et al. ..... Plt. 74

P.P. 6,143 4/1988 van der Jagt ..... Plt. 74

*Primary Examiner*—Howard J. Locker

*Attorney, Agent, or Firm*—Foley & Lardner

[57] ABSTRACT

A Chrysanthemum plant named Cumbia particularly characterized by its flat capitulum form; daisy capitulum type; dark red-purple ray floret color; diameter across face of capitulum of 95 to 108 mm when fully opened, when grown as a single stem spray cut mum; flowering response in Salinas under normal temperatures is 50 to 57 days after start of short days; flowering response in Bogota, Colombia under temperatures of minimum 6.3 degrees Celsius night and maximum 29 degrees Celsius day is 65 to 72 days; plant height is 99 to 119 cm when grown in Salinas with 6 to 7 long days prior to start of short days; and 107 to 132 cm with grown in Bogota with 7 to 17 long days prior to start of short days; peduncle length of the first lateral at flowering after removing the apical bud without growth regulator applications is 10 to 20 cm when grown in Salinas, and 13 to 15 cm when grown in Bogota; peduncle length of the fourth lateral at flowering is 15 to 25 cm when grown both in Salinas, and 18 to 23 cm when grown in Bogota; many of the ray floret tips are double indented, with the petal tips being strongly convex; large, very attractive deeply lobed and strongly serated foliage; and excellent tolerance to low night temperatures for bud initiation and flower development.

3 Drawing Sheets

The present invention comprises a new and distinct cultivar of Chrysanthemum, botanically known as *Dendranthema grandiflora*, and referred to by the cultivar name Cumbia.

Cumbia, identified as 2495 (87-505001), was originated from a cross made by Cornelis P. VandenBerg in a controlled breeding program in Salinas, Calif., in July 1986.

The female parent of Cumbia was an unnamed seedling, identified as 6031 (82-J20111), and described as a red-bronze spooned daisy cut spray mum having a flowering response to short days of 60 to 63 days when grown in Salinas, Calif., and 72 to 84 days when grown in Bogota, Colombia; a plant height of 86 to 114 cm when grown with 14 long days prior to start of short days in Salinas, Calif., and 112 to 137 cm with 14 long days prior to start of short days when grown in Bogota, Colombia; and a diameter of capitulum of 70 to 76 mm. The female parent was discarded from all trials flowering programs in February 1986, and was discarded completely after completion of the seed production program which eventually led to the discovery and selection of Cumbia.

The male parent of Cumbia was an unnamed seedling, identified as 1033 (83-715009), and described as a white flat daisy spray cut mum having a flowering response to short days of 55 to 64 days in Salinas, Calif., and 80 days in Bogota, Colombia; and a plant height of 69 to 89 cm with 7 to 14 long days prior to start of short days when grown in Salinas, Calif. The diameter of capitulum of the male parent of Cumbia was not recorded. The male parent of Cumbia was tested only twice in Colombia and was discarded from the Colombian program in November 1985, because of very slow flowering response, and was discarded copmletely from all programs in September 1987.

Cumbia was discovered and selected as one flowering plant within the progeny of the stated cross by Cornelis P. VandenBerg in January 1988, in Salinas, Calif.

The first act of asexual reproduction of Cumbia was accomplished when vegetative cuttings were taken from the initial selection in March 1988 in a controlled environment in Salinas, Calif., by technicians working under supervision of Cornelis P. VandenBerg.

Horticultural examination of controlled flowerings of successive plantings has shown that the unique combination of characteristics as herein disclosed for Cumbia are firmly fixed and are retained through successive generations of asexual reproduction.

Cumbia has not been observed under all possible environmental conditions. The phenotype may vary significantly with variations in environment such as temperature, light intensity and daylength.

The following observations, measurements and comparisons describe plants grown in Salinas, Calif., and in Bogota, Colombia, under greenhouse conditions which approximate those generally used in commercial greenhouse practice. The low temperature tolerance was determined in repeated flowerings in Bogota, Colombia, with an average minimum low night temperature inside the greenhouse during our trials ranging from 6.3 to 10.0 degrees Celsius.

The following traits have been repeatedly observed and are determined to be basic characteristics of Cumbia, which, in combination, distinguish this Chrysanthemum as a new and distinct cultivar:

1. Flat capitulum form.
2. Daisy capitulum type.

3. Dark red-purple ray floret color.
4. Diameter across face of capitulum of 95 to 108 mm when fully opened, when grown as a single stem spray cut mum.
5. Flowering response in Salinas under normal temperatures is 50 to 57 days after start of short days. Flowering response in Bogota, Colombia under temperatures of minimum 6.3 degrees Celsius night and maximum 29 degrees Celsius day is 65 to 72 days.
6. Plant height is 99 to 119 cm when grown in Salinas with 6 to 7 long days prior to start of short days; height is 107 to 132 cm when grown in Bogota with 7 to 17 long days prior to start of short days.
7. Peduncle length of the first lateral at flowering after removing the apical bud without growth regulator applications is 10 to 20 cm when grown in Salinas, and 13 to 15 cm when grown in Bogota. Peduncle length of the fourth lateral at flowering is 15 to 25 cm when grown in Salinas, and 18 to 23 cm when grown in Bogota.
8. Many of the ray floret tips are double indented, with the petal tips being strongly convex.
9. Large, very attractive deeply lobed and strongly serrated foliage.
10. Excellent tolerance to low night temperatures for bud initiation and flower development.

The accompanying photographic drawings show typical inflorescence and leaf characteristics of Cumbia, with the colors being as nearly true as possible with illustrations of this type.

Sheet 1 is a color photograph of Cumbia grown as a single stem spray cut mum in Salinas, Calif.

Sheet 2 is a black and white photograph of three views of the inflorescence of Cumbia.

Sheet 3 is a black and white photograph showing the upper and under sides of the leaves of Cumbia at 3 stages of development (mature, intermediate and immature). In sheets 2 and 3 a measuring tape in centimeters has been added.

Of the commercial cultivars known to the inventor, the most similar to comparison to Cumbia is the cultivar identified as Accent, disclosed in U.S. Plant Pat. No. 3,945. Reference is made to attached Chart A, which compares certain characteristics of Cumbia to the same characteristics of Accent.

Similar traits are ray floret color (although the color of Cumbia is slightly darker than the color of Accent), capitulum form and type, flowering response to short days when grown in Salinas, Calif., and spray formation. Cumbia has a much larger diameter of capitulum when compared with Accent, much more vigor, and longer peduncles. The low vigor of Accent requires at least 14 long days prior to start of short days to obtain a commercially acceptable height, while Cumbia only requires 6 to 7 days or less to obtain acceptable plant height. Accent has a very poor low night temperature tolerance and can not be grown commercially under the environmental conditions of Bogota, Colombia, while Cumbia has excellent tolerance to the Bogota low night temperatures.

When compared with both parents, Cumbia has a significantly faster flowering response in Colombia than either parent. In addition, both parents were discarded from all programs because of overall unsatisfactory performance worldwide, while the overall performance of Cumbia in the USA and Colombia warrants commercial introduction.

In the following description color references are made to The Royal Horticultural Society Colour Chart. The color values were determined on plant material grown as a single stem spray cut mum in Salinas, Calif., on Jun. 26, 1990.

Classification:

*Botanical.*—*Dendranthema grandiflora* cv Cumbia.

*Commercial.*—Daisy spray cut mum.

INFLORESCENCE

A. Capitulum:

*Form.*—Flat.

*Type.*—Daisy.

*Diameter across face.*—95 to 108 mm when fully opened.

B. Corolla of ray florets:

*Color (general tonality from a distance of three meters).*—Dark red-purple.

*Color (upper surface).*—70A to 70B.

*Color (under surface).*—75A to 75C.

*Shape.*—Many tips of ray florets are double indented; bases of ray florets are concave, outer ray florets are longitudinally convex, and the tips of the ray florets are strongly convex.

C. Corolla of disc florets:

*Color (mature).*—12A.

*Color (immature).*—12A, overlaid with 144B.

D. Reproductive organs:

*Androecium.*—Present on disc florets only; moderate pollen.

*Gynoecium.*—Present on both ray and disc florets.

PLANT

A. General appearance:

*Height.*—99 to 119 cm when grown in Salinas with 6 to 7 long days prior to start of short days, and 107 to 132 cm when grown in Bogota with 7 to 17 long days prior to start of short days.

B. Foliage:

*Color (upper surface).*—147A.

*Color (under surface).*—147B.

*Shape.*—Large, very attractive, deeply lobed and strongly serrated. See photograph.

CHART A

COMPARISON OF CUMBIA AND ACCENT

| CHARACTERISTIC | CUMBIA | ACCENT |
|---|---|---|
| Ray floret color | Dark red-purple | Dark red-purple |
| Capitulum form and type | Flat daisy | Flat daisy |
| Diameter across face of capitulum | 95 to 108 mm | 70 to 91 mm |
| Flowering response: | | |
| in Salinas | 50 to 57 days | 50 to 57 days |
| in Bogota | 65 to 72 days | not available |
| Plant height: | | |
| 6–7 long days Salinas | 99 to 119 cm | |
| 14 long days Salinas | | 58 to 102 cm |
| Peduncle length: | | |
| 1st lateral Salinas | 10 to 20 cm | 3 to 10 cm |
| 4th lateral Salinas | 15 to 25 cm | 13 to 20 cm |
| Spray formation | Terminal | Terminal |
| Low night temperature tolerance | Excellent | Poor |

COMPARISONS MADE OF PLANTS GROWN AS SINGLE STEM SPRAY CUT MUMS IN SALINAS, CALIFORNIA

I claim:

1. A new and distinct Chrysanthemum plant named Cumbia, as described and illustrated.

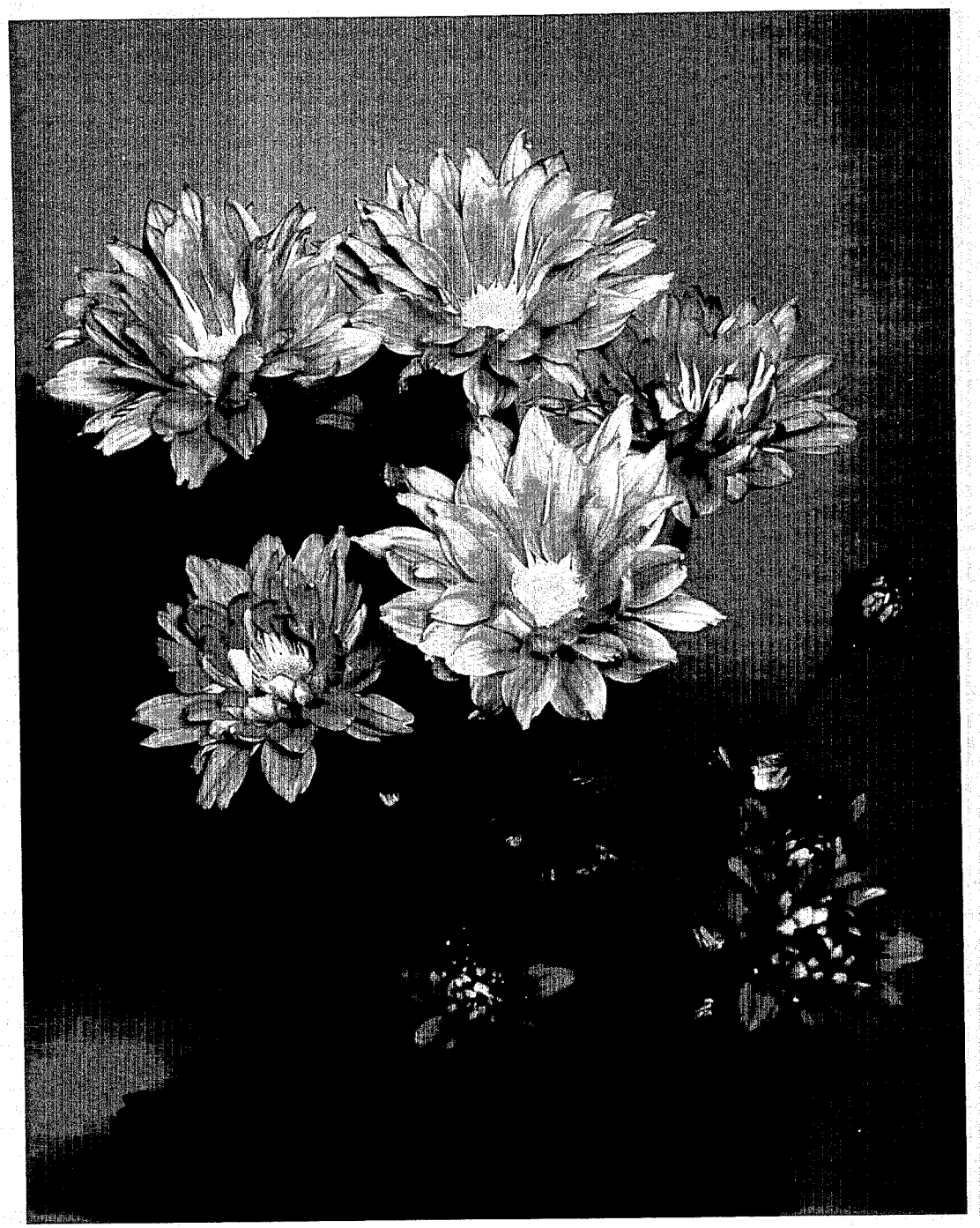

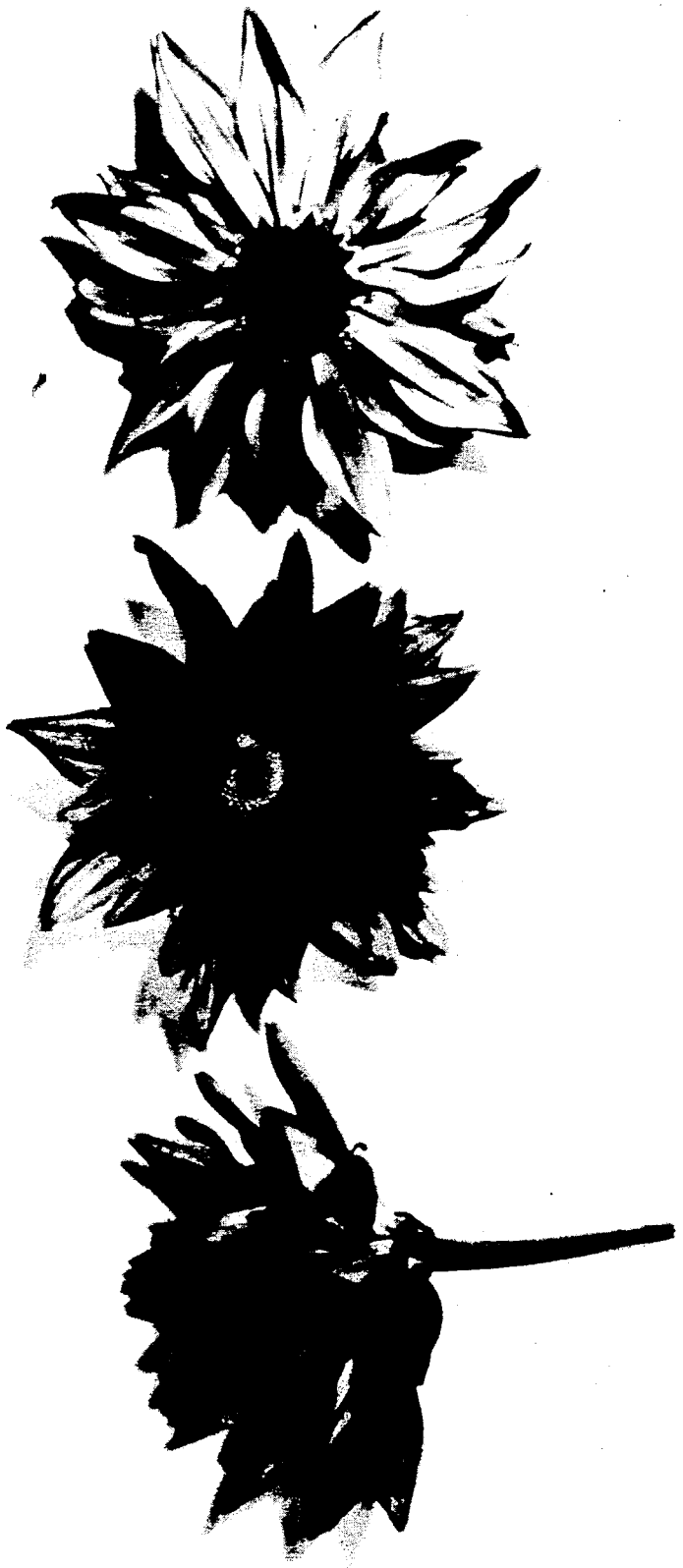

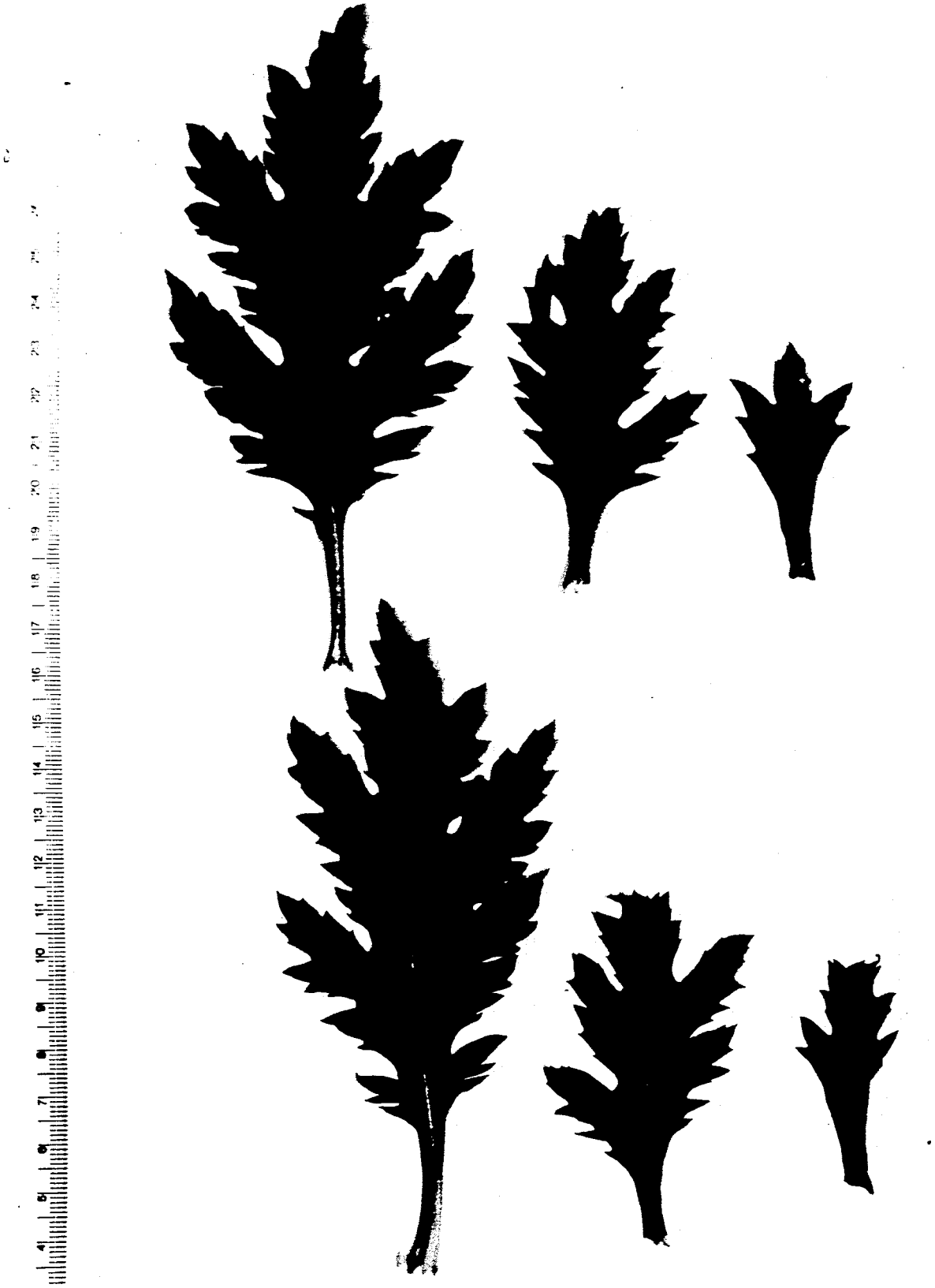

* * * * *